United States Patent
Dietl

(10) Patent No.: US 11,266,786 B2
(45) Date of Patent: Mar. 8, 2022

(54) STOPPER FOR A MEDICAMENT CONTAINER

(71) Applicant: Carebay Europe Ltd., Sliema (MT)

(72) Inventor: Thomas Dietl, Falkenfels (DE)

(73) Assignee: SHL MEDICAL AG, Zug (CH)

( * ) Notice: Subject to any disclaimer, the term of this patent is extended or adjusted under 35 U.S.C. 154(b) by 344 days.

(21) Appl. No.: 15/752,445

(22) PCT Filed: Jul. 6, 2016

(86) PCT No.: PCT/EP2016/065971
§ 371 (c)(1),
(2) Date: Feb. 13, 2018

(87) PCT Pub. No.: WO2017/025253
PCT Pub. Date: Feb. 16, 2017

(65) Prior Publication Data
US 2019/0009034 A1    Jan. 10, 2019

(30) Foreign Application Priority Data
Aug. 13, 2015  (SE) .................... 1551070-4

(51) Int. Cl.
*A61M 5/315* (2006.01)
(52) U.S. Cl.
CPC ............ *A61M 5/31513* (2013.01); *A61M 2005/31521* (2013.01)
(58) Field of Classification Search
CPC .......... A61M 5/31513; A61M 5/31515; A61M 2005/31516; A61M 5/31521;
(Continued)

(56) References Cited

U.S. PATENT DOCUMENTS

| 4,266,557 A | 5/1981 | Merry |
| 4,543,093 A * | 9/1985 | Christinger ....... A61M 5/31513 604/228 |

(Continued)

FOREIGN PATENT DOCUMENTS

| DE | 2514412 A1 | 10/1976 |
| EP | 0815885 A1 | 1/1998 |

OTHER PUBLICATIONS

English Translation of Abstract of German Patent Application No. 2514412 dated Feb. 12, 2018, 1 page.

*Primary Examiner* — Brandy S Lee
(74) *Attorney, Agent, or Firm* — McDonnell Boehnen Hulbert & Berghoff LLP

(57) ABSTRACT

A stopper for use within a medicament container, preferably a plastic container, is presented having a main body defining an open distal end and a closed proximal end, where the main body has a longitudinal axis L. A cup shaped tip portion is integrally formed with the main body adjacent the closed proximal end and a distally extending flexible skirt extends from a distal end outer surface of the main body, where the distally extending flexible skirt has a rib which extends radially outward around a perimeter of the distally extending flexible skirt. A proximally extending flexible skirt extends from a proximal end outer surface of the main body, where the proximally extending flexible skirt has at least two ribs which extend radially outward around a perimeter of the proximally extending flexible skirt and that are axially spaced apart along the proximally extending flexible skirt.

18 Claims, 3 Drawing Sheets

(58) Field of Classification Search
CPC .............. A61M 5/31523; A61M 5/315; A61M 5/31511; A61M 2005/31521; A61K 8/9728; A61K 8/9789
See application file for complete search history.

(56) References Cited

U.S. PATENT DOCUMENTS

| | | | | |
|---|---|---|---|---|
| 5,181,912 | A * | 1/1993 | Hammett | A61M 5/5066 |
| | | | | 604/110 |
| 5,496,285 | A | 3/1996 | Schumacher et al. | |
| 6,224,577 | B1 * | 5/2001 | Dedola | A61M 5/31513 |
| | | | | 604/218 |
| 7,727,202 | B2 | 6/2010 | Kirchhofer et al. | |
| 8,475,415 | B2 | 7/2013 | Schiller et al. | |
| 2006/0293687 | A1 * | 12/2006 | Bogert | A61B 17/8825 |
| | | | | 606/92 |
| 2008/0300550 | A1 | 12/2008 | Schiller et al. | |
| 2008/0300551 | A1 * | 12/2008 | Schiller | A61M 5/31513 |
| | | | | 604/220 |
| 2011/0034882 | A1 * | 2/2011 | Quinn | A61M 5/31513 |
| | | | | 604/218 |
| 2011/0204097 | A1 * | 8/2011 | Buehler | A61M 5/31513 |
| | | | | 222/386 |
| 2012/0253291 | A1 | 10/2012 | Ivosevic et al. | |
| 2015/0148751 | A1 * | 5/2015 | Yotsutsuji | A61M 5/31513 |
| | | | | 604/218 |
| 2016/0082193 | A1 * | 3/2016 | Laubach | A61M 5/31513 |
| | | | | 604/222 |
| 2016/0287800 | A1 * | 10/2016 | Nakano | B29C 59/16 |

* cited by examiner

STOPPER FOR A MEDICAMENT CONTAINER

CROSS REFERENCE TO RELATED APPLICATIONS

The present application is a U.S. National Phase Application pursuant to 35 U.S.C. § 371 of International Application No. PCT/EP2016/065971 filed Jul. 6, 2016, which claims priority to Swedish Patent Application No. 1551070-4 filed Aug. 13, 2015. The entire disclosure contents of these applications are hereby incorporated by reference into the present application.

TECHNICAL FIELD

The invention relates to a stopper for use with a medicament container and, more particularly, to a stopper having a positive displacement feature for use with a pre-filled plastic medicament container and associated plunger rod.

BACKGROUND

Known stopper designs comprise front and back seals and are characterized by a constant diameter seal and a constant stopper-container interference to create a seal that will prevent enclosed fluid in a container from leaking past the front seal. It is also known that the contact pressure of the seals with the wall of the container has to be high enough such that the fluid will not leak under the highest fluid pressure inside the container when the stopper is subjected to an axial force. However, a higher contact pressure leads to higher static and dynamic frictional forces. The static friction force is commonly known as a break loose force. It has also been found that even when controlling the tolerances required for obtaining the desired seal between the stopper wall and the container wall to prevent bypass or leakage of the fluid during a stroke, an easy and smooth movement of the stopper is problematic. Also known is the phenomenon of reflux, which is the reversal of fluid flow up through the catheter, usually due to the spring back of the stopper in the distal direction at the end of a flush injection, which is a result of the bottoming out of the stopper at the proximal end of the medicament container at the end of dose delivery.

Document U.S. Pat. No. 5,496,285 describes a disposable medicament container comprising, inter alia, a piston produced from a thermoplastically processable rubber mixture. The piston is delimited in the direction of the medical agent by a peripheral sealing lip that contacts the inside surface of the hollow cylinder and that can be deflected in the radial direction. The sealing lip can have at least one sealing edge that is delimited on the outside by two conical surfaces that intersect one another. The nose projection located at the proximal end of the piston partially fills the outlet opening of the hollow cylinder, such projection is consequently deformed and unsuitable for preventing leakage.

Document U.S. Pat. No. 7,727,202 describes a piston stopper for a medicine injector, wherein the stopper has a stopper body with a mesh section and at least one sealing element, both made of different materials working as threaded sections. The sealing element is a sealing ring positioned in a circumferential recess or groove. There is no projection at the stopper body forward end. Hence, medicine material may not be entirely expelled and a small quantity will necessarily remain in the passage between the medicament container medicament container and the cannula resulting in undesired reflux.

Document U.S. Pat. No. 8,475,415 discloses a stopper adapted for attachment with a plunger rod for use within a medicament container. The stopper includes an integrated main body and a core member. The core member comprises a nose portion having a profile adapted to seal the outlet opening of such medicament container in order to prevent reflux. A lip seal is depicted in one embodiment of the stopper formed by a flexible arm, which is radially deflected as sealing pressure increases. Moreover, deflection occurs upon insertion of the stopper within the medicament container medicament container to form an air pocket to trap an air bubble, which assists in the anti-reflux capabilities of the stopper. However, this device requires an additional axial movement of the plunger rod to attain a complete deflection of the nose portion of the stopper for bottoming out the front part of the medicament container leading to material losses.

SUMMARY

It is an object of the present invention to provide a stopper for use with a medicament container, preferably a plastic container, which is characterized by novel features of construction for providing an effective seal between the stopper and the inner surface of the medicament container and which is easy to activate when it is subjected to a stroke, thus reducing the degree of deflection required on the stopper body. The stopper of the present disclosure can be manufactured by a unique molding process which is easy and economical.

In a preferred embodiment of the invention, the stopper may have an unique and distinctive configuration including a circumferentially extending axially directed sealing or wiper lip, which may project outwardly at a predetermined lead angle less than 90 degrees relative to the longitudinal axis of the stopper, more preferably less than ten degrees, and most preferably approximately three degrees relative to a longitudinal axis, when the stopper is in the relaxed state outside the medicament container.

In a preferred embodiment, the stopper and the medicament container may be made of dissimilar materials to provide greater lubricity between the stopper and the medicament container, which may contribute to easy movement and prevention of galling. The medicament container may be made of a clear plastic, such as a cyclic olefin copolymer (COC). The stopper may be made of a fluoro polymeric plastic. Typically, in known assemblies a rubber piston is used with a plastic or glass medicament container. The glass containers are not tolerance sensitive since an external lubricant is usually applied to the piston before use to facilitate relatively easy of the piston within the glass medicament container. Plastic stoppers are also known and are less expensive to manufacture, but generally present tolerance problems. For example, it has been found that small tolerance variations from one assembly to the next can make a large change in how smoothly the stopper rides in the medicament container when activated.

The goal of the present invention is to obtain the proper balance between a constant diameter seal and a break loose force in order to prevent leakage, lower the friction force and decrease the degree of deflection on the stopper body.

This goal is achieved according to the present invention by providing a stopper according to the features of the appended independent patent claim. The stopper of the present disclosure is preferably for use within a plastic medicament container, the stopper comprising a main body defining an open distal end and a closed proximal end, the main body extending along a longitudinal axis L; a cup shaped tip portion is integrally formed with the main body adjacent the closed proximal end; a distally extending flexible skirt extends from a distal end outer surface of the main body, where the distally extending flexible skirt comprises a rib which extends radially outward around a perimeter of the distally extending flexible skirt; a proximally extending flexible skirt extends from a proximal end outer surface of the main body, where the proximally extending flexible skirt comprises at least two ribs which extend radially outward around a perimeter of the proximally extending flexible skirt and are axially spaced apart along the proximally extending flexible skirt.

In a preferred embodiment of the invention, the stopper comprises ribs adapted for contacting with an inner surface of the medicament container to form an active seal. The ribs ensure that a constant seal pressure is maintained against the internal wall of the medicament container, enhancing the seal tolerance when the stopper with the attached plunger rod is moved axially.

In another embodiment, the main body of the stopper has an outer surface between the skirts, where the outer surface is configured to be positioned at a predetermined radial distance inward and away from the perimeter of the skirt ribs and also the inner surface of the medicament container. This predetermined distance of the outer surface minimizes the area of contact of the skirts with the medicament container to reduce the static friction of the skirts with respect to the medicament container and thereby reducing break-loose force.

According to still another aspect of the invention, the forward or proximally extending skirt is configured to form at least one closed pocket to create a positive fluid pressure chamber therein. The closed pocket acts as a positive pressure chamber increasing the sealing effect on the proximal inner end of medicament container at the completion of the dose delivery.

According to yet another aspect of the invention, the main body of the stopper includes one or more inner surfaces having a curved contour from a sidewall portion of the main body to the core member and wherein the inner surface of the main body is configured to contact and engage with a connector, preferably a taper, on the forward (proximal) end of a plunger rod to apply a radial force to the medicament container upon the application of a forward force in the proximal direction to the plunger rod.

The closed proximal end of the stopper may comprise a hollow circumferential projection nose having a diameter smaller than the diameter of the main body. Such construction will decrease the reflux effect when bottoming out the stopper at the distal inner surface of the container.

The features, functions, and advantages that have been discussed can be achieved independently in various embodiments or may be combined in yet other embodiments, the further details of which can be seen with reference to the following description and drawings.

BRIEF DESCRIPTION OF THE FIGURES

The present disclosure will become more fully understood from the more detailed description presented below and the accompanying drawings which are presented by way of illustration only, and thus, are not limitations of the present disclosure, and wherein.

Corresponding parts are marked with the same reference symbols in all figures.

DETAILED DESCRIPTION

In the present application, when the term "distal part/end" is used, this refers to the part/end of a stopper, or the parts/ends of the members thereof, which is/are located the furthest away from a medicament delivery site of the patient. Correspondingly, when the term "proximal part/end" is used, this refers to the part/end of the stopper, or the parts/ends of the members thereof, which, is/are located closest to the medicament delivery site of the patient.

Figure 1:
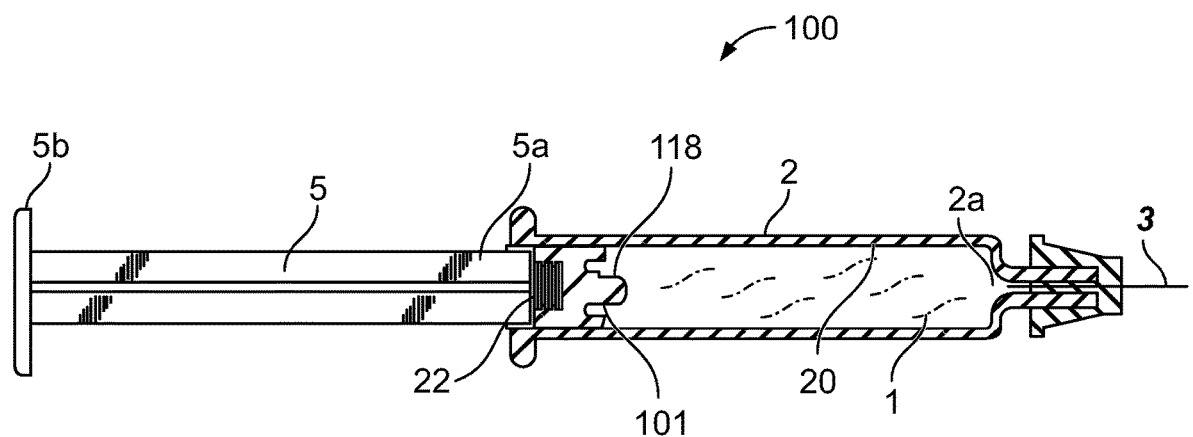
FIG. 1 shows a longitudinal view in cross section of the main parts of a conventional disposable medicament container known in the art.

Reference is made now to FIG. 1. The device of FIG. 1 generally represents a known disposable pre-filled medicament device 100, wherein a disposable medicament container 2 is filled with a liquid medicinal agent 1. The disposable medicament container 2 comprises a hollow cylinder, one axial end of which is closed off in a liquid-tight manner by a conventional piston 101 placed on the proximal end 5a of a plunger rod 5 via connector 22, and the other axial end of medicament container 2, which is provided with an injection needle 3. A projection nose 118 is located at the proximal end of the piston 101 that at least partially fills the inner outlet opening 2a of the hollow cylinder or plastic medicament container 2.

Figure 2:
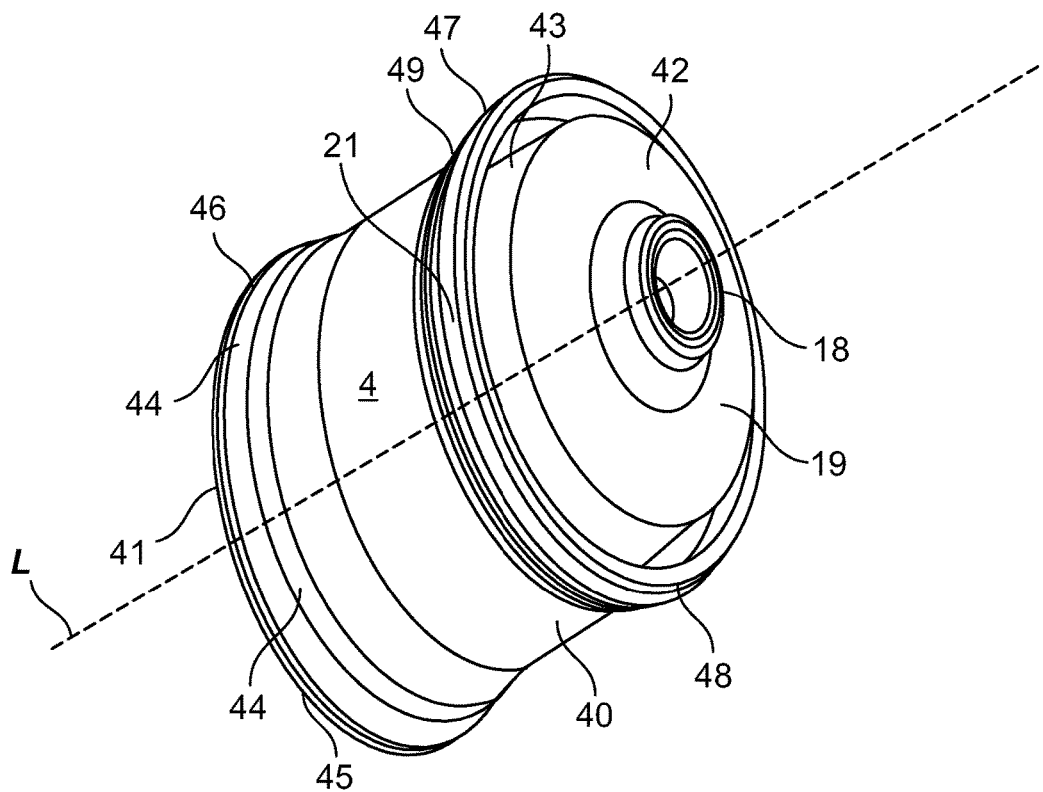
FIG. 2 shows a perspective view of a stopper according to a first embodiment of the invention.
Figure 3:
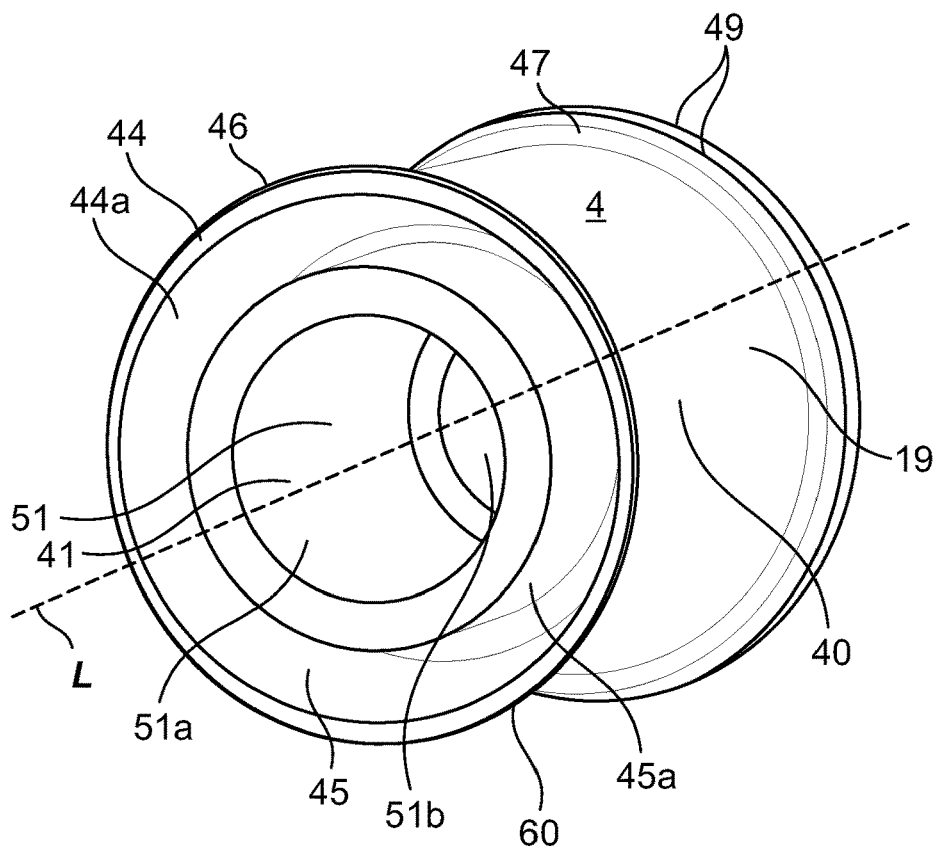
FIG. 3 shows a second perspective view of a stopper according to a first embodiment of the invention.

FIGS. 2 & 3 depict stopper 4 of the present disclosure in different perspective views. Stopper 4 can be used in a medicament container, such as the medicament device 100 illustrated in FIG. 1, where stopper 4 of the present disclosure replaces conventional piston 101. Stopper 4 can be located at the proximal end 5a of the plunger rod 5, preferably by using connector 22 to secure the stopper 4 to the plunger rod 5. Connector 22 can be a tapered fitting, a screw fitting, a snap lock fitting or a friction fitting. Once connected, these two components interact as a single component, since the proximal end 5a of plunger rod 5 is embedded in and/or connected at the open distal end 41 of a main body 40 and into hollow cavity 51 defined by inner walls 51a and 51b. The stopper 4 moves forward in the proximal direction within the medicament container 2 by a force applied by the user on distal end 5b of the plunger rod 5.

Figure 5:
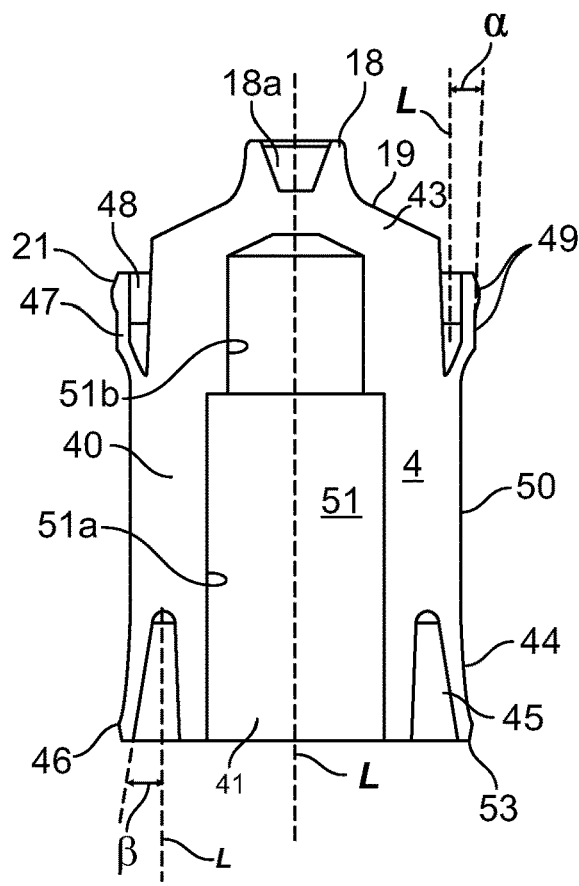
FIG. 5 shows a cross-sectional view of the stopper of FIG. 2.

The stopper 4 is for use within a medicament container 2; preferably one made of plastic. Stopper 4 comprises a main body 40 defining an open distal end 41 and a closed proximal end 42. The main body 40 extends along a longitudinal axis L of the stopper 4. The stopper 4 may have a unique and distinctive tip configuration defined by core member 19, including a circumferentially extending axially directed sealing or wiper lip 21 that defines the proximal end of a flexible proximal extending skirt 47. Wiper lip 21 may project outwardly at a predetermined lead angle α (see FIG. 5) to contact inner surface 20 of medicament container 2. This radial projection is desirable and is a result of the materials of construction of the skirt 47, which can be formed as an integral part of main body 40 or could also be co-molded using a different material of construction than that used for main body 40. In other words, the material of construction used to form the skirt 47 (and also skirt 44) can be selected such that when the stopper 4 is in the relaxed state as illustrated in FIG. 5, the skirt or skirts (44, 47) are naturally biased radially outward by the angles α and/or β. The lead angle α is preferably less than 90 degrees (901, more preferably less than ten degrees (101, and most preferably approximately 6.33 degrees (6.33) as measured relative to the axis L of main body 40 of stopper 4 in a relaxed, non-moving and non-pressurized state. Such a state exists when the stopper 4 is outside of the medicament container 2. The angled projection of skirt 47 defines a pocket 48 between the inner surface of the skirt 47 and main body 40. Pocket 48 is configured to create a positive fluid pressure chamber therein.

The stopper 4 also comprises a cup shaped tip portion 43 integrally formed with the main body 40 adjacent the closed proximal end 42. This construction allows for a complete bottoming out of the closed proximal end 42 into the front inner outlet opening part 2a of the medicament container 2.

Moreover, as illustrated in FIG. 3, the stopper 4 comprises a distally extending flexible skirt 44, which extends from a distal end outer surface 60 of the main body 40 and defines pocket 45. Pocket 45 is defined by an inner skirt wall 44a and an inner distal body wall 45a. As shown in FIG. 5, the distally extending flexible skirt 44 comprises a rib 46 arranged around a perimeter of the distally extending flexible skirt 44, where the skirt 44 projects radially from the longitudinal axis L by an angle β, resulting in an increased peripheral sealing lip 53. Angle β is less than 90 degrees (901, preferably greater than angle α, and most preferably greater than 10 degrees (101 as measured relative to the axis L of main body 40 of stopper 4 in a relaxed, non-moving and non-pressurized state. A most preferred angle β is 12 degrees (12'). Skirts 44 and 47 are configured to flex radially inward toward main body 40, thus decreasing angle α and/or angle β as the stopper 4 is inserted into and contacts the container walls and when the stopper is moved within the container during the operational state as the plunger rod 5 pushes and exerts an axial force on stopper 4 in the proximal direction causing it move or slide within medicament container 2.

Figure 4:
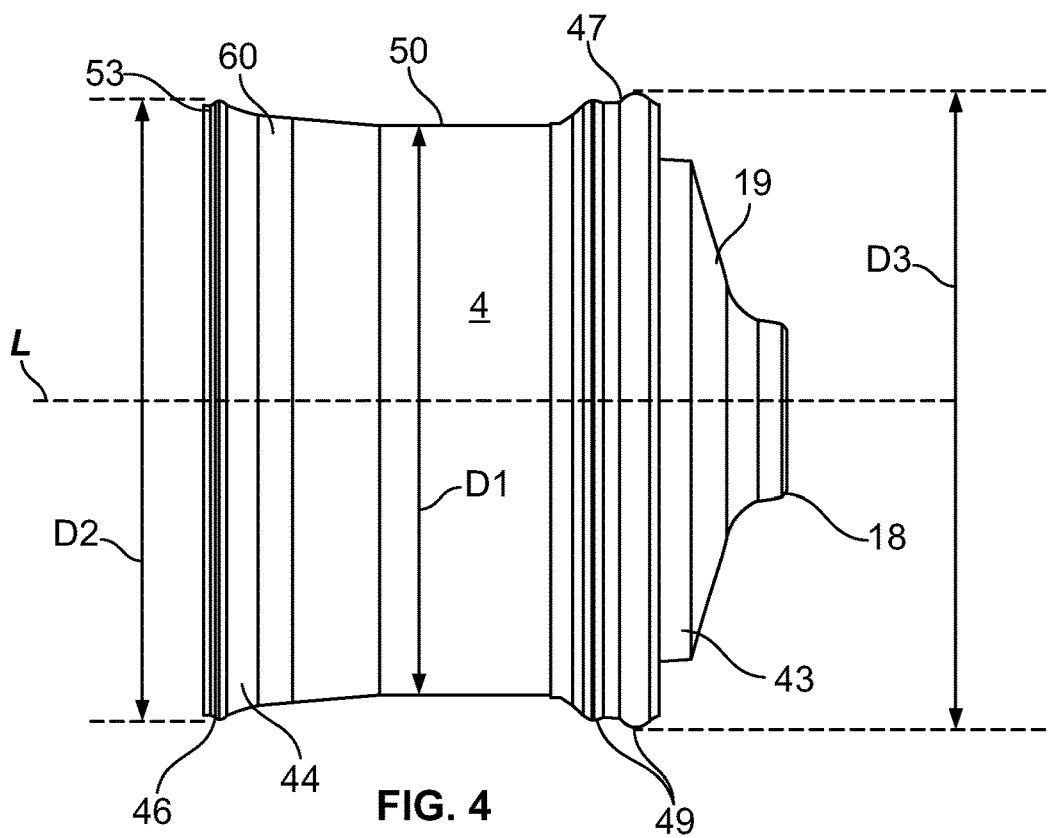
FIG. 4 illustrates a side view of the stopper of FIG. 2.

FIG. 4 illustrates a side view of the stopper 4 showing the proximally extending flexible skirt 47 extending from a proximal end outer surface of the main body 40. The proximally extending flexible skirt 47 comprises at least two ribs 49, which extend radially outward around a perimeter of the proximally extending flexible skirt 47, such ribs 49 are axially spaced apart along the proximally extending flexible skirt 47. The periphery or perimeter of ribs 46, 49 define diameters D2 and D3, respectively. The outer surface 50 defines a diameter D1, where preferably D1 is less than D2 and D3. D3 is typically greater than D2 when the stopper 4 is in a relaxed state outside of container 2. A small amount of compression takes place when stopper 4 is inserted into the container such that D2 and D3 become approximately the same. Stopper 4 when provided with skirts 44, 47, as described above, allows stopper 4 to achieve a secured sealing engagement between the inner surface 20 of medicament container 2 and the stopper 4 as it slides axially in the proximal direction during dispensing of medicinal agent 1 from medicament container 2. This sealing engagement prevents the medicament from flowing in the distal direction as the plunger rod 5 and connected stopper 4 are pushed forward in the proximal direction.

Figure 6:
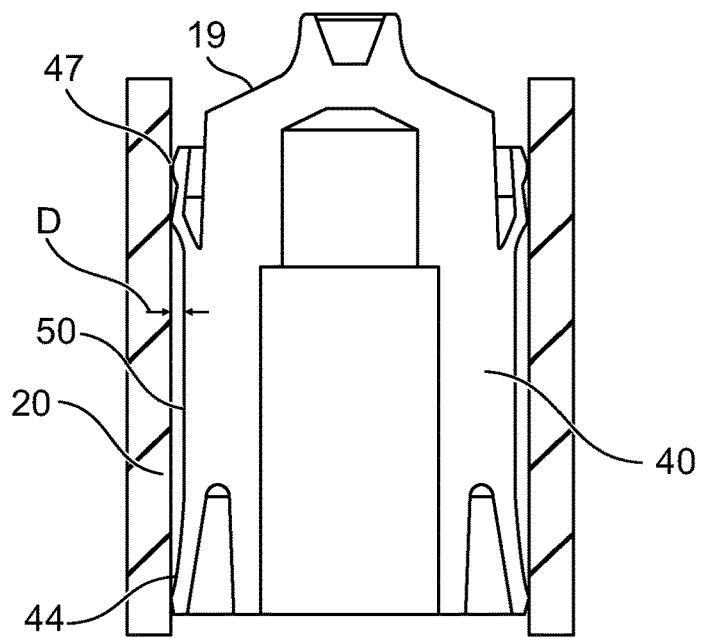
FIG. 6 shows a cross-sectional view of the stopper of FIG. 2 inside a medicament container.

The sealing engagement is enhanced by the presence of the ribs 46, 49 on the outer periphery of skirts 44 & 47, respectively, as shown in FIG. 5, which presents a cross-sectional view of a stopper 4 in its relaxed, non-compressed state outside of container walls. Ribs 46, 49 are adapted for contacting with the inner surface 20 of the medicament container 2 as shown in FIG. 6 and thereby assisting in the formation of the active seal described above. In this way, no leakage in the distal direction in the medicament container 2 will occur since the liquid material or medicinal agent 1 is expelled by the seal pressure between the ribs 46, 49 and internal walls or inner surface 20 of medicament container 2.

The stopper main body 40 has an outer surface 50 between the skirts 44 and 47. The outer surface 50 is positioned a predetermined distance D away from the inner surface 20 of the medicament container 2 to minimize the area of contact of the skirts 44, 47 with the inner wall 20 of medicament container 2. (see FIG. 6). This minimization of contact area reduces the static friction between the skirts 44, 47 and the inner wall 20 of the medicament container 2, thereby reducing the break-loose force required to set the stopper 4 in axial motion.

The stopper main body 40 also includes an inner cavity 51 defined by a curved contour from a sidewall portions 51a and 51b of the main body 40 that extends to the core member 19. Preferably, sidewall portion 51b has a smaller internal diameter than sidewall portion 51a. The inner surface 51a and/or 51b is configured for contact and attachment with connector 22, which is preferably a tapered connector, on the forward (proximal) end 5a of the plunger rod 5 to apply a radial force through stopper 4 to seal and contain the medicinal agent 1 within the medicament container 2 upon the application of a forward driving force to the distal end 5b of plunger or piston rod 5.

The stopper 4 has closed proximal end 42 that is shaped to include a hollow circumferential projection nose 18 having a smaller diameter than the main body 40. Projection nose 18 has a central cavity 18a that allows projection nose 18 to flex and conform to the proximal inner outlet opening surface 2a of medicament container 2. A minimal deflection of projection nose 18 is required by application of an axial force on plunger rod 5 transmitted through the inner cavity 51 of the stopper 4 to cause projection nose 18 to bottom out against the proximal inner outlet opening surface 2a of the medicament container 2. This bottoming out creates a pressure in the proximal direction directed through injection needle 3 that prevents reflux and minimizes the amount of liquid medicinal agent that will remain within the medicament container at the end of the plunger rod stroke, i.e., at the conclusion of the medicament delivery.

Furthermore, in the claims, the word "comprising" does not exclude other elements or steps, and the indefinite article "a" or "an" does not exclude a plurality. A single unit may fulfill the functions of several features recited in the claims. The terms "essentially", "about", "approximately" and the like in connection with an attribute or a value particularly also define exactly the attribute or exactly the value, respectively. Any reference signs in the claims should not be considered as limiting the scope.

It is however to be understood that embodiments described above and shown in the drawings are to be regarded only as non-limiting examples of the present invention and that may be modified within the scope of the appended patent claims. As such, the foregoing description of the specific embodiments are intended to reveal the general nature of the disclosure so others can, by applying current knowledge, readily modify and/or adapt for various applications such specific embodiments without departing from the generic concept, and therefore such adaptations and modifications are intended to be comprehended within the meaning and range of equivalents of the disclosed embodiments. Moreover, the phraseology or terminology used herein is for the purpose of description and not of limitation.

What is claimed:

1. A stopper for use within a medicament container, the stopper comprising:
   a main body defining an open distal end and a closed proximal end, the main body having a longitudinal axis L and an outer surface defining a first diameter;
   a projection nose extending proximally from the closed proximal end of the main body, wherein the projection nose defines a hollow central cavity including an opening at a proximal-most end of the projection nose;
   a distally extending flexible skirt extending from the open distal end of the main body, wherein the distally extending flexible skirt comprises a first rib which extends radially outward around a perimeter of the distally extending flexible skirt and defines a second diameter; and
   a proximally extending flexible skirt extending from the closed proximal end of the main body, wherein the proximally extending flexible skirt comprises a second rib and a third rib that each extend radially outward around a perimeter of the proximally extending flexible skirt, wherein the second rib and the third rib are axially spaced apart along the proximally extending flexible skirt, wherein the second rib and the third rib are both positioned proximal to a connection point between the proximally extending flexible skirt and the main body, wherein at least one of the second rib and the third rib both define a third diameter, wherein the first diameter is less than the second diameter and the third diameter, wherein the third diameter is greater than the second diameter when the stopper is in a relaxed state outside of the medicament container, and wherein the third diameter comprises a maximum diameter of the stopper.

2. The stopper according to claim 1, wherein the distally extending flexible skirt extends from a distal end outer surface of the main body.

3. The stopper according to claim 1, wherein the proximally extending flexible skirt extends from a proximal end outer surface of the main body.

4. The stopper according to claim 1, wherein the proximally extending flexible skirt comprises an integral part of the main body.

5. The stopper according to claim 4, wherein a diameter of the projection nose is smaller than the first diameter of the main body.

6. The stopper according to claim 1, wherein each of the ribs has an outer periphery configured to contact an inner surface of the medicament container to form an active seal.

7. The stopper according to claim 1, wherein the outer surface is located between the distally extending flexible skirt and the proximally extending flexible skirt, wherein the outer surface is positioned a predetermined radial distance away from an outer periphery of the ribs to minimize an area of contact of the main body with an inner surface of the medicament container to reduce static friction between the distally extending flexible skirt and the proximally extending flexible skirt and the inner surface of the medicament container and to reduce break-loose force.

8. The stopper according to claim 1, wherein the proximally extending skirt is configured to form a pocket that creates a positive fluid pressure chamber when the stopper is moved axially in a proximal direction within the medicament container.

9. The stopper according to claim 1, wherein the main body includes an inner cavity having a curved contour surface formed from a sidewall portion of the main body.

10. The stopper according to claim 9, wherein the inner cavity is configured to accept and connect a forward end of a plunger rod such that an axial force applied to the plunger rod in a proximal direction causes a radial force to be applied to the stopper such that the proximally extending flexible skirt engages an inner surface of the medicament container.

11. The stopper according to claim 1, wherein the proximally extending flexible skirt projects radially outward from the longitudinal axis L by an angle α.

12. The stopper according to claim 11, wherein angle α is less than about 10 degrees.

13. The stopper according to claim 11, wherein the distally extending flexible skirt projects radially outward from the longitudinal axis L by an angle β.

14. The stopper according to claim 13, wherein angle β is greater than angle α.

15. The stopper according to claim 1, further comprising a core member comprising a circumferentially extending axially directed sealing lip.

16. The stopper according to claim 1, wherein the main body includes an inner cavity including a first sidewall portioned at a distal end of the inner cavity and a second sidewall portion positioned at a proximal end of the inner cavity, and wherein a diameter of the first sidewall portion is greater than a diameter of the second sidewall portion.

17. The stopper according to claim 16, wherein the first diameter is constant along an entire length of the first sidewall portion, and wherein the second diameter is constant along an entire length of the second sidewall portion.

18. The stopper according to claim 1, wherein a diameter of the hollow central cavity of the projection nose decreases from the opening to a distal end of the hollow central cavity such that a shape of the hollow central cavity is a truncated cone.

* * * * *